United States Patent
Spierings

(10) Patent No.: US 6,669,733 B1
(45) Date of Patent: Dec. 30, 2003

(54) BONE PLUG

(76) Inventor: Petrus Tarasius Josephus Spierings, Madoerastraat 24, 6524 LH Nijmegen (NL)

(*) Notice: Subject to any disclaimer, the term of this patent is extended or adjusted under 35 U.S.C. 154(b) by 0 days.

(21) Appl. No.: 09/831,718

(22) PCT Filed: Nov. 12, 1999

(86) PCT No.: PCT/NL99/00695

§ 371 (c)(1),
(2), (4) Date: Jul. 18, 2001

(87) PCT Pub. No.: WO00/28926

PCT Pub. Date: May 25, 2000

(30) Foreign Application Priority Data

Nov. 12, 1998 (NL) .............................................. 1010539

(51) Int. Cl.$^7$ ............................. A61F 2/28; A61B 17/60
(52) U.S. Cl. ....................................... 623/23.48; 606/95
(58) Field of Search ...................... 606/95; 623/23.48, 623/23.23, 23.26

(56) References Cited

U.S. PATENT DOCUMENTS

| | | | |
|---|---|---|---|
| 5,531,792 A | * 7/1996 | Huene | 623/23.47 |
| 5,862,861 A | 1/1999 | Kalsi | 166/277 |
| 6,235,058 B1 | * 5/2001 | Huene | 623/13.14 |
| 6,251,141 B1 | * 6/2001 | Pierson et al. | 623/23.48 |

FOREIGN PATENT DOCUMENTS

| | | |
|---|---|---|
| DE | 1006107 | 11/1993 |
| EP | 0058744 | 9/1982 |
| FR | 2708192 | 2/1995 |
| FR | 2763500 | 11/1998 |
| GB | 2324731 | 5/1997 |
| WO | WO9846173 | 10/1998 |

* cited by examiner

Primary Examiner—Nicholas D. Lucchesi
Assistant Examiner—Fenn C Mathew
(74) Attorney, Agent, or Firm—Milde & Hoffberg, LLP

(57) ABSTRACT

A bone plug (61), for blocking of a canal in a bone, has a solid body which by axial compression expands in the radial direction. The height of the body is at most 6 times the average wall thickness of the body. The body (65) is preferably made out of an elastomeric material.

Figure 1:
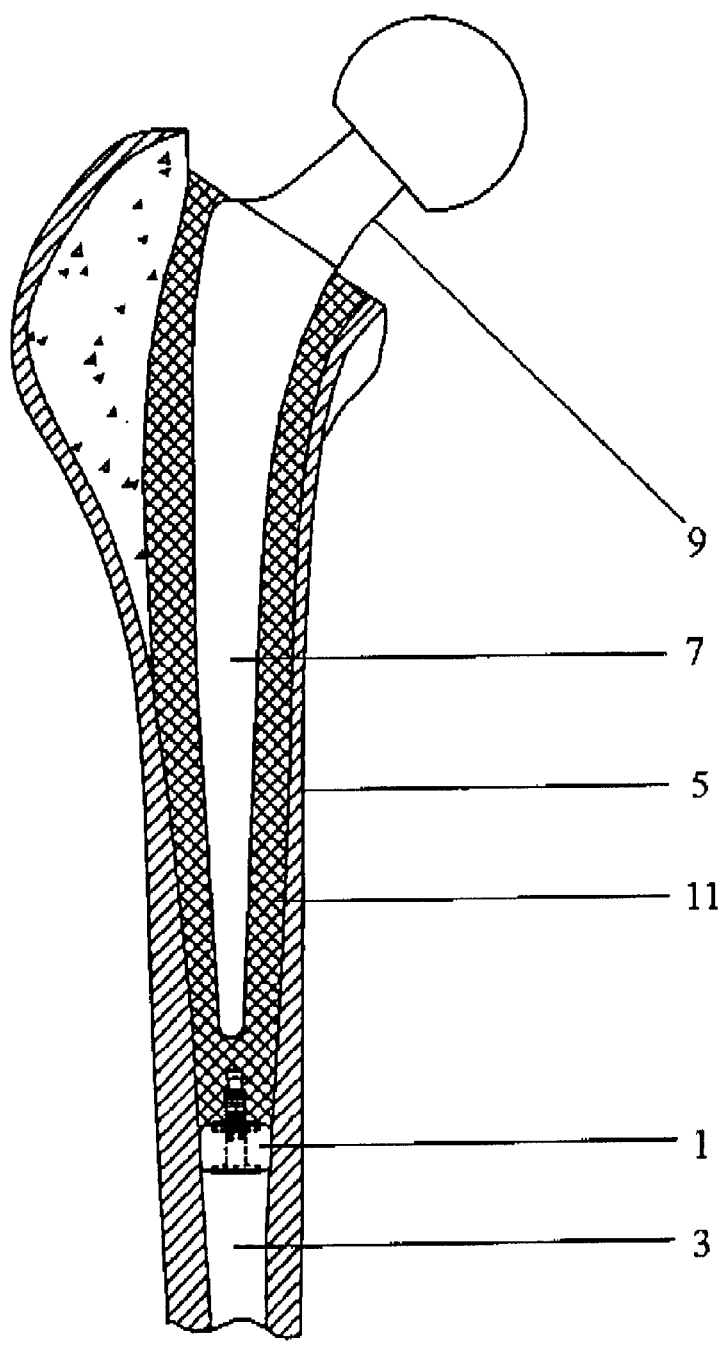

For keeping the body (65) axially locked the bone plug comprises a first locking element (67) which is formed by a disc (69) with attached to it a stem (71) provided with saw tooth shaped protrusions (73) which protrudes through an axial opening in the body (65) and a second locking element (75) which is formed by an interrupted ring (77) and an annular plate (79), which are positioned around the stem (71). The ring (77) locks behind one of the protrusions (73) and the annular plate (79) is positioned between the interrupted ring (77) and the body (65).

Fixating of the bone plug (61) in the canal is carried out by pushing the interrupted ring (77) along the stem (71) until it locks behind one of the protrusions.(73), whereby the body (65) is compressed between the plate (79) and the disc (69) and expands in radial direction and gets fixed in the bony canal.

16 Claims, 7 Drawing Sheets

BONE PLUG

FIELD OF THE INVENTION

The invention relates to a bone plug, for blocking of a canal in a bone, comprising a radially expandable blocking element which comprises an at least nearly solid body, which body under axial compression expands into radial direction and is provided with a continuous axial opening, which body has a height and an average wall thickness along said height, which bone plug comprises means to keep the body in expanded condition locked in the axial direction, which means comprise two locking elements which can be fixed on various distances to each other, in between which the body with its axial boundaries is positioned, of which a first locking element comprises a stem which is provided with a number of radial protrusions which are positioned next to each other in axial direction on the stem, which stem protrudes through the axial opening of the body, whereby the second locking element is positioned around the stem and can hook behind the protrusions. With the height of the body is meant the size of the body in the longitudinal direction of the stem. The term—"average wall thickness along the height"—is used, to be able to bename the wall thickness in case of non cylindrical shapes of the body like for example a cambered shape.

Bone plugs are used in the medical field for permanent or temporarily blocking of a canal in a long bone. For fixating of an endoprosthesis or artificial joint, for example an artificial hip prosthesis, in a bone, a stem of the prosthesis is inserted in the intramedullary canal of a long bone which is filled with bone cement. In order to prevent the bone cement to protrude in the canal any further than necessary for fixating of the stem and to assure that the bone cement is only present between the stem and the endosteal wall of the bone and to prevent leaking of the bone cement any further into the intramedullary canal, the canal beneath the stem is blocked with a bone plug.

BACKGROUND OF THE INVENTION

A bone plug of the abovementioned type is known from the French patent publication FR-A-2708193. The body of the known bone plug is made out of a flexible, resorbable, biocompatible material which under axial compression expands into radial direction. The body of the blocking element of the known bone plug is slim and has in relation to the height a minor wall thickness. In practice it has shown that such ratio of the sizes of the body are unsuitable in order to obtain a sufficient large radial expansion of the body. At such large axial compression the body will fold and crumple instead of expanding in radial direction, which is adversable for obtaining a good blocking of the canal in a bone. Hence the use of the known bone plug for blocking of canals is of limited value.

SUMMARY OF THE INVENTION

Part of the invention is to provide a bone plug of the kind described in the introduction, which is better than the known bone plug. Therefor the bone plug according to the invention is characterized in that the height of the body is at most 8 times the average wall thickness of the body. With this ratio between the height and the wall thickness, the body will also evenly expand in radial direction in case of large axial compression and will not crumple up in an irregular manner. Hereby the range of application is considerably larger than of the known bone plug. Preferred embodiments of the bone plug according to the invention are characterized in that the height of the body is at most 7, 6 or 5 times the average wall thickness, and in practice a suitable value has shown to be nearby 5.

A bone plug of the abovementioned type is known from the French patent publication FR-A-2708192. The body of the known bone plug is made out of a flexible, resorbable, biocompatible material which under axial compression expands into radial direction. The body of the blocking element of the known bone plug is slim and has in relation to the height a minor wall thickness. In practice it has shown that such ratio of the sizes of the body are unsuitable in order to obtain a sufficient large radial expansion of the body. At such large axial compression the body will fold and crumple instead of expanding in radial direction, which is endosteal wall.

An embodiment of the bone plug according to the invention is characterized in that the radial protrusions are located at least nearly to each other in the longitudinal direction of the stem. This makes compression of the body possible in smaller steps than with the known bone plug, where the protrusions are positioned on a relatively large distance to each other. By this possibility of accurate control of the amount of compression of the body, the bone plug can better be installed in a canal and a canal can better be blocked than with the known bone plug. Preferably the radial protrusions have an at least nearly saw-tooth shape in a longitudinal section of the stem.

It is noted that a bone plug with a stem with protrusions, which are positioned near to each other in the axial direction of the stem, is known from patent publication DE-A-92 13120.4. However a fully different shape of the body has been applied here. Experience showed that in particular by a combination of a solid body with a stem provided with protrusions which are positioned near to each other, a well functioning bone plug is obtained.

It is noted that the beneficial effect of the fact that the protrusions are positioned near to each other also occurs when the ratio between the height of the body and the average wall thickness does not fulfil the abovementioned condition, by which explicitly the possibility is preserved to claim this feature separately from the feature that the height of the body is at most 6 times the average wall thickness of the body.

A further embodiment of the bone plug according to the invention is characterized in that the material of the body of the blocking element has at least nearly elastomeric properties. A body of an elastomeric material is nearly incompressible, whereby the axial compression is nearly fully converted in a radial expansion without loss of volume. In case of the known bone plug an axial compression will in contrary not only result in a radial expansion, but the body itself is also compressed, which means that the volume decreases. Hereby, the bone plug according to the invention will, at equal axial compression, achieve a larger radial expansion than the known bone plug and the bone plug according to the invention will better be fixed in the canal than the known bone plug.

It is noted that the beneficial effect of a body of an elastomeric material also occurs when the ratio between the height and the average wall thickness does not fulfil the aforementioned condition by which explicitly the possibility is preserved to claim this feature separately from the feature that the height of the body is at most 6 times the average wall thickness of the body.

A preferred embodiment of the bone plug according to the invention is characterized in that the material of the body of the blocking element is composed mainly from a mixture of gelatine, glycerine and water. It is noted that a material composed from a mixture of gelatine, glycerine and water is known on itself and that it is known to use such a material for the production of bone plugs. This known application for bone plugs however is only used in order to obtain a flexible material which is biologically degradable. Hereby no advantage is made of the specifically for the type of bone plug according to the invention, beneficial incompressible properties of the material.

It is also noted that the beneficial effect of the fact that the material of the body of the blocking element is composed mainly of a mixture of gelatine, glycerine and water also occurs when the ratio between the height and the average wall thickness of the body does not fulfil the aforementioned condition, by which explicitly the possibility is preserved to claim this feature separately from the feature that the height of the body is at most 6 times the average wall thickness of the body.

A further embodiment is characterized in that the material of the locking elements is mainly made out of polymethylmethacrylate. Also the bone cement which is applied in the intramedullary canal of a bone is mainly made out of polymethylmethacrylate. Hereby the bone cement becomes during its polymerization process chemically bonded to the locking elements and will form one solid piece. This will facilitate any future revision procedures when the bone cement and the bone plug have to be removed.

The second locking element of the known bone plug is formed by an elastic ring which expands in radial direction when it is pushed over a protrusion and which contracts again behind the protrusion. The known ring therefor has to be sufficient stiff to remain locked behind the protrusion while being pressed upon by the body. Through this a relatively large force is needed to push the ring over the protrusions during installation of the known bone plug. This is not beneficial for an accurate and proper installation of the known bone plug. In order to eliminate this disadvantage, a further embodiment of the bone plug according to the invention is characterized in that the second locking element comprises an interrupted ring. Hereby the ring can be pushed with moderate force over the protrusions and it is better secured that the ring will remain locked behind the protrusions.

It is noted that the beneficial effect of the fact that the second locking element comprises an interrupted ring also occurs when the ratio between the height and the average wall thickness does not fulfil the aforementioned condition, by which explicitly the possibility is preserved to claim this feature separately from the feature that the height of the bone plug is at most 6 times the average wall thickness of the body.

In order to keep the body of the blocking element better locked between the locking elements, a further embodiment of the bone plug according to the invention is characterized in that the second locking element also comprises an annular shaped plate which is positioned between the body and the interrupted ring. In this manner the interrupted ring can optimally be designed to lock behind the protrusions on the stem while the annular shaped plate fulfils the function of locking the body.

In order to prevent loosening of the interrupted ring an embodiment is characterized in that the annular shaped plate contains a recession in which the interrupted ring is positioned. By shaping the recession such that the interrupted ring is locked in place, the interrupted ring no longer can bend open and therefor can not come loose.

A practical beneficial embodiment of this is characterized in that the interface between the outer diameter of the interrupted ring and the wall of the recession is bevelled. Preferably the interrupted ring has a triangular cross-section.

A further embodiment of the bone plug according to the invention is characterized in that the stem is hollow and at least at the free end is open. This hole can be used to position a prosthetic component. A prosthetic component which is provided with a tip which fits accurately in the hole of the stem can be reproducibly positioned relative to the intramedullary canal by inserting the tip in the hole of the stem.

A further embodiment which is useful for temporarily fixating an instrument in the intramedullary canal, is characterized in that the stem of the first locking element is provided at its free end with a screw thread. The stem for example is provided with an internal screw thread into which the instrument can be screwed.

These last applications can also be realised with an embodiment with a solid stem provided with an external screw thread or providing the prosthetic component with a hole hich fits accurately around the stem. However in practice it has shown advantageous when an instrument or prosthetic component is respectively fixed or positioned inside the stem instead of around the stem.

Finally a further embodiment is characterized in that the stem of the first locking element has a weakened spot near to its free end. This weak spot can for example be formed by construction of the stem or by a groove in the stem. During installation of the bone plug the second locking element is kept immobile by an insertion instrument while simultaneously the insertion instruments pulls at the stem of the first locking element. Hereby the body is compressed in the axial direction and the stem will break when the instrument pulls too hard. This will cause that the maximum compression force on the body is in all cases nearly the same and sufficient to obtain a strong fixation of the expanded body inside the canal. In order to prevent the stem to fracture near a protrusion, the stem is deliberately weakened near the free end which is pulled upon by the insertion instrument.

DETAILED DESCRIPTION OF THE DRAWINGS

Figure 2:
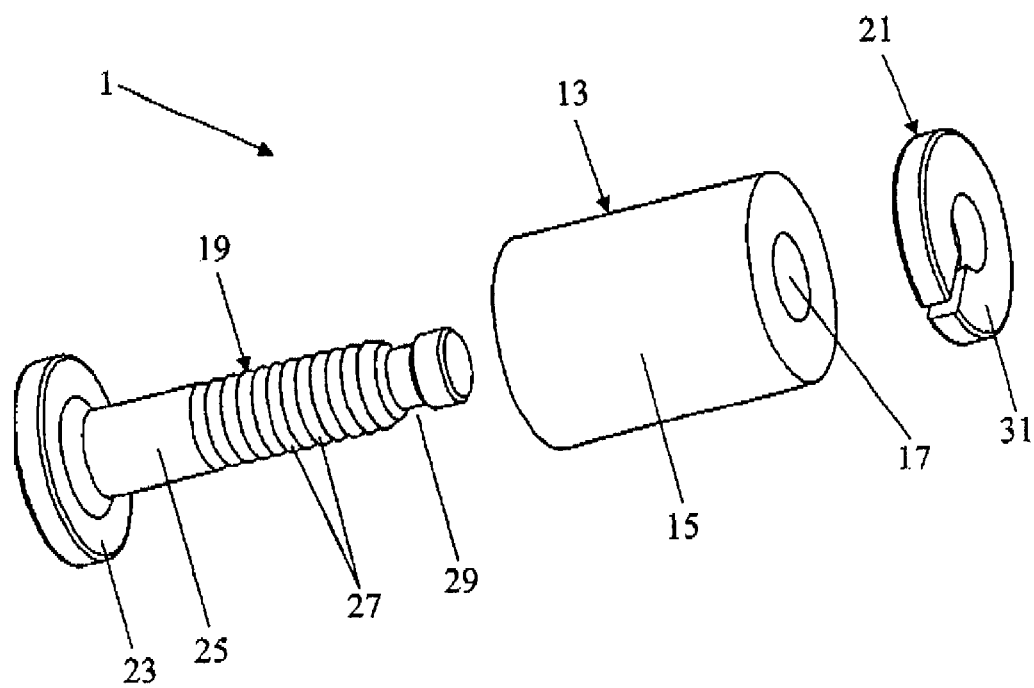
Figure 3:
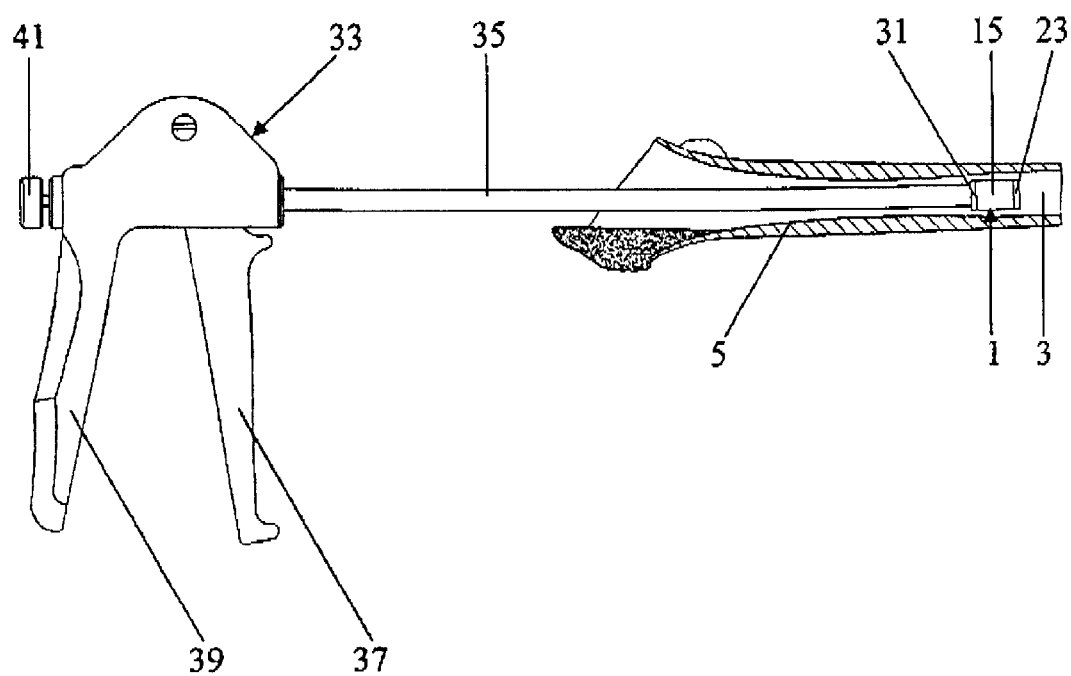
Figure 4:
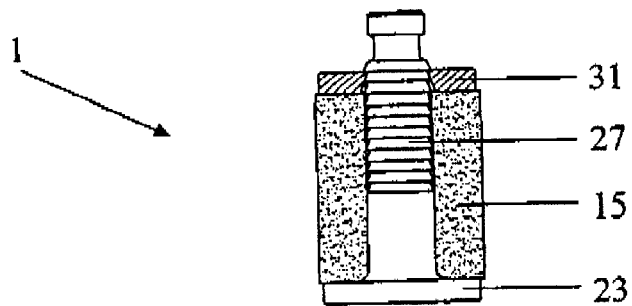
Figure 5:
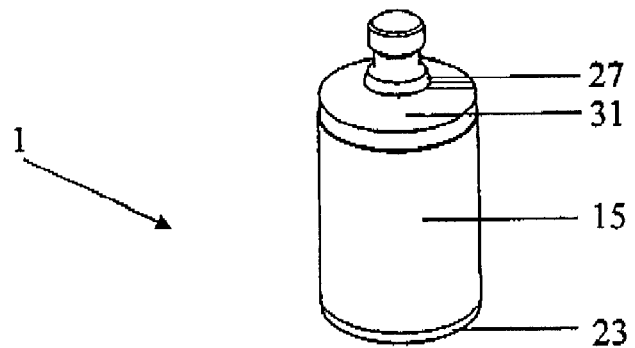
Figure 6:
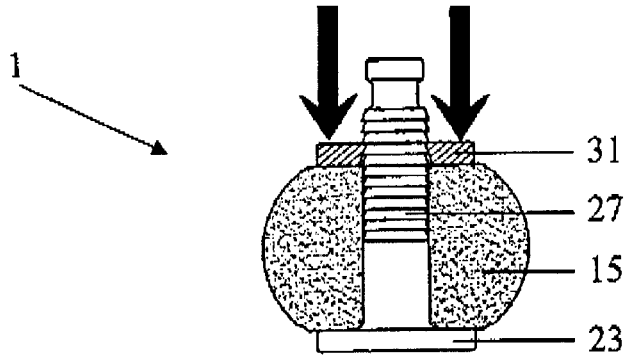
Figure 7:
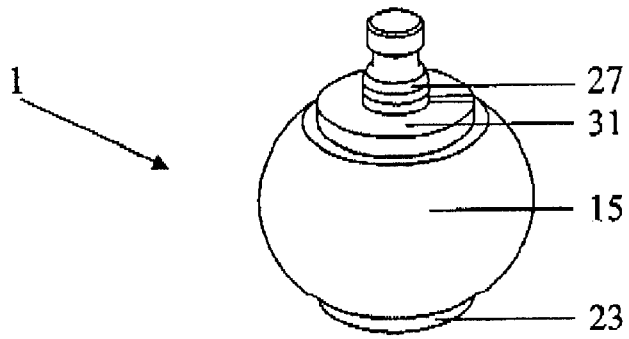
Figure 8:
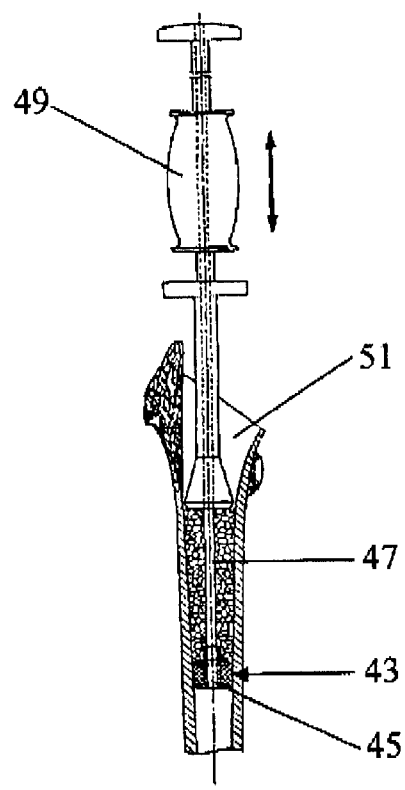
Figure 9:
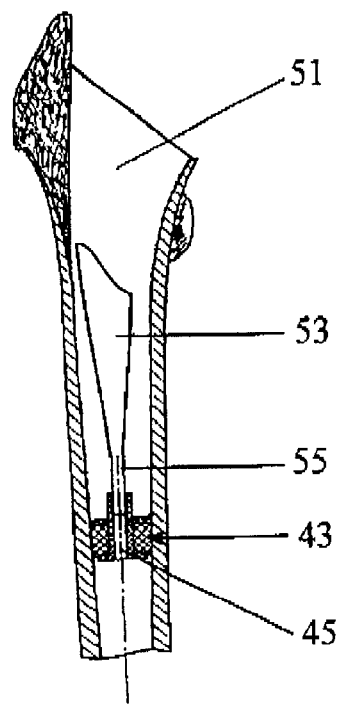
Figure 10:
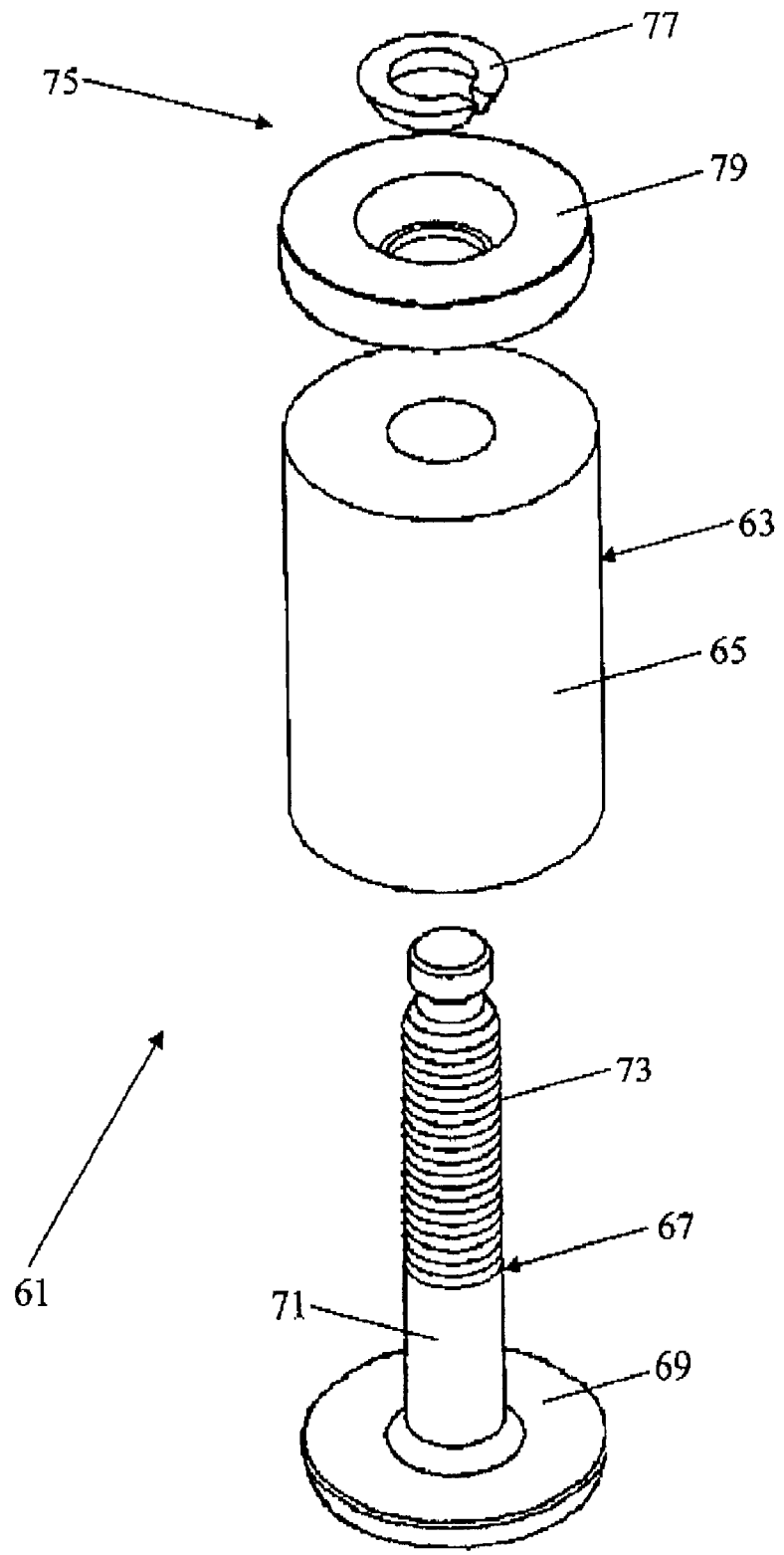
Figure 11:
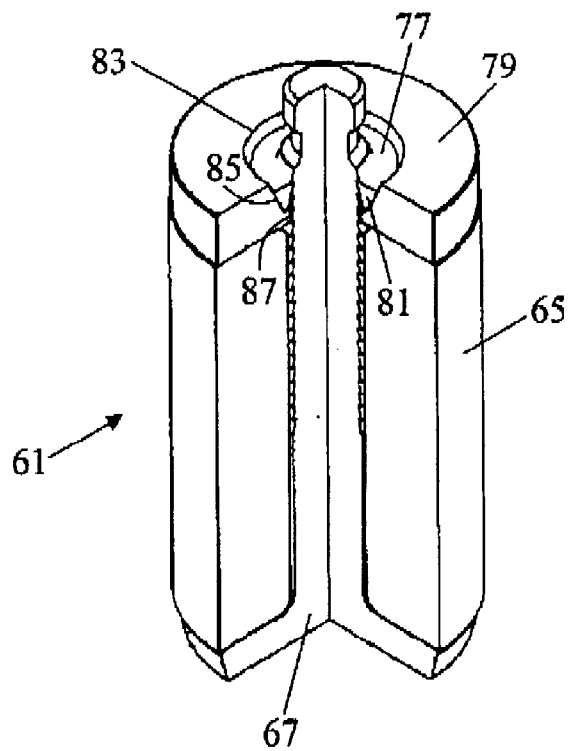
Figure 12:
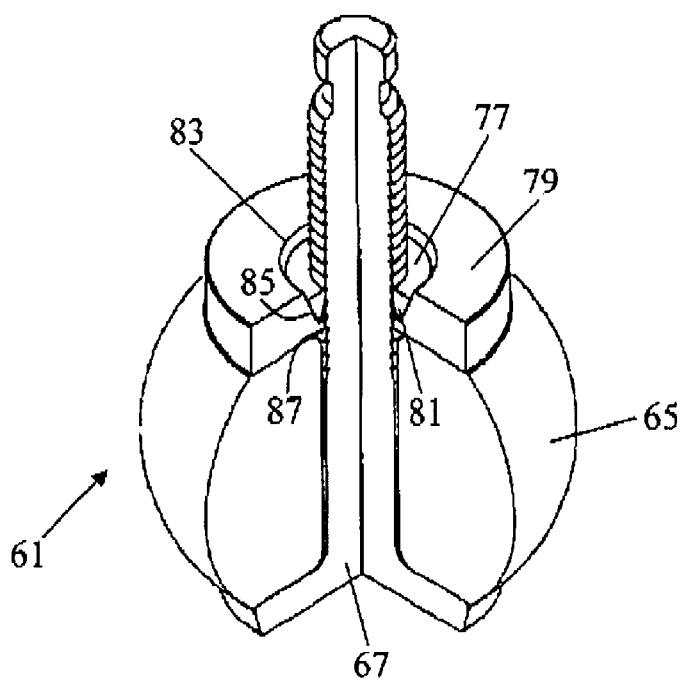
Figure 13:
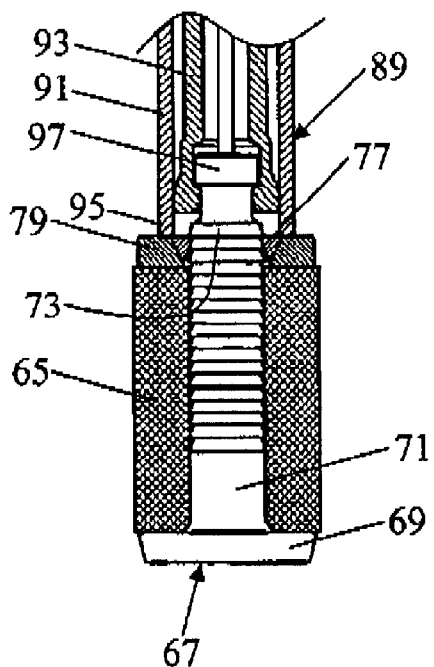
Figure 14:
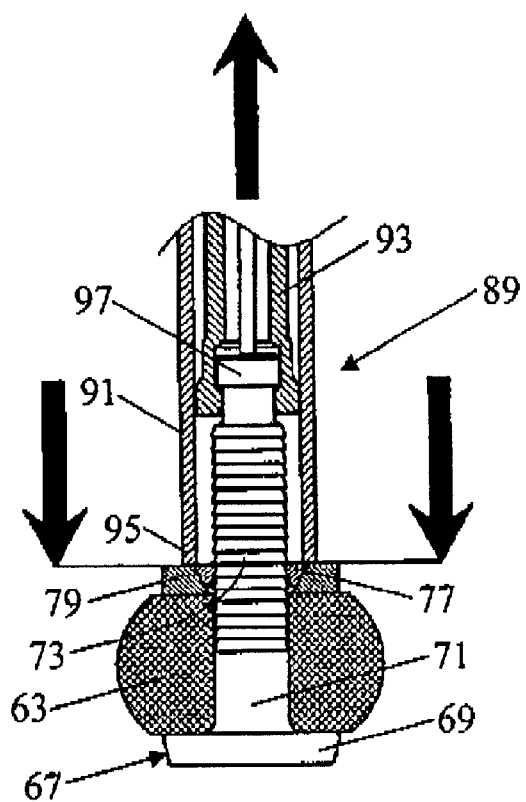

Hereafter the invention shall be explained in more detail by means of a preferred embodiment which is shown in the drawings. Thereby shows:

FIG. 1 a first embodiment of the bone plug according to the invention positioned inside the intramedullary canal of a bone in which a prosthesis is fixated by means of bone cement;

FIG. 2 the various parts of the bone plug;

FIG. 3 the insertion of the bone plug by means of an insertion instrument;

FIG. 4 a longitudinal section of the bone plug in a non-compressed condition;

FIG. 5 a perspective view of the bone plug in a non-compressed condition;

FIG. 6 a longitudinal section of the bone plug in a compressed condition;

FIG. 7 a perspective view of the bone plug in a compressed condition;

FIG. 8 a second embodiment of the bone plug according to the invention which is used to temporarily fixate an instrument inside the bony canal;

FIG. 9 a second embodiment of the bone plug in a canal for positioning of a prosthetic component inside the bony canal;

FIG. 10 a third embodiment of the bone plug according to the invention in parts in a perspective view;

FIG. 11 a partly exploded perspective view of the bone plug shown in FIG. 10 in the non-compressed condition;

FIG. 12 a partly exploded perspective view of the bone plug shown in FIG. 10 in the compressed condition;

FIG. 13 a longitudinal section of the bone plug shown in FIG. 10 fixed in an instrument in the non-compressed condition; and FIG. 14 a longitudinal section of the bone plug shown in FIG. 10 fixed in an instrument in the compressed condition.

DETAILED DESCRIPTION OF THE DRAWINGS

In FIG. 1 a bone plug 1 according to the invention is shown inside the canal 3 of a bone 5 to clarify the possibilities for application of a bone plug. Inside bone 5 a stem 7 of a prosthesis is fixated by bone cement 11. Hereby it is not advisable to fill the entire canal with bone cement but only the complete space between the prosthetic stem and the bone has to be filled with bone cement. Hence the intramedullary canal is blocked by means of a bone plug before the bone cement and the prosthesis are inserted. The bone plug is inserted at the requested depth in the canal and expanded at that position in the radial direction of the canal by which the bone plug becomes fixated inside the canal. The bone plug 1 is shown in parts in detail in FIG. 2. The bone plug 1 comprises a blocking element 13 which is formed by a cylindrical body 15 provided with a continuous axial opening 17 and made out of an elastomeric material. The body 15 is composed of a mixture of gelatine, glycerine and water which is biologically degradable. The body 15 will expand in radial direction while being compressed in axial direction and will nearly not be compressed in a way that the volume decreases. In order to be able to block the most common canal diameters a number of three sizes of bone plugs with values for the height and the wall thickness of the body of 23 respectively 5.5 mm, 17 respectively 3.5 mm and 12 respectively 2.5 mm will suffice. Of course numerous other sets of values are possible.

The bone plug 1 further has means to be able to lock the body 15 in an expanded condition. These means are formed by two locking elements 19 and 21. The first locking element 19 comprises a disc 23 with a stem 25 attached to the centre of the disc, which is provided with a number of saw tooth shaped protrusions 27 and a circumferential recession 29 nearby the free end of the stem. The second locking element 21 comprises an interrupted ring 31. The locking elements 19 and 21 are preferably made out of polymethylmethacrylate (PMMA).

In the assembled condition the stem 25 protrudes through the opening 17 and the ring 31 is situated around the stem 25 and is locked behind one of the protrusions 27. The body 15 is in the assembled condition of the bone plug locked between the disc 23 and the ring 31.

The recession 29 makes a weak spot in stem 25 which on the one hand enables a firm grip on the stem 25 during insertion of the bone plug 1 and on the other hand assures that stem 25 will only fracture at that recession 29 during compression of the body 15. The installation of the bone plug 1 can be carried out with an insertion instrument. FIG. 3 shows insertion of the bone plug 1 by means of an insertion instrument 33. The insertion instrument 33 has a chuck (not shown in figure) with which stem 25 is fixed nearby the recession 29. The chuck is axially movable in a tube 35 of the insertion instrument 33. The free end of tube 35 is in contact with ring 31 of the bone plug 1. By pulling handle 37 towards grip 39, the chuck is pulled further into the tube 35. Ring 31 is stopped by the free end of tube 35. Hereby the stem 25 is pulled further through the ring 31, which will lock behind one of the following protrusions 27. The body 15 which is positioned between the disc 23 and the ring 31 is compressed in the axial direction. Hereby the body 15 will expand in radial direction up to the inner wall of the bone and will get fixed in the canal 3, like it is shown in FIG. 1. Stem 25 is pulled so hard upon until it fractures at the weak spot of the recession 29. Then the insertion instrument 33 is extracted from the canal and the fractured head is removed by opening the chuck by pushing button 41. The body will expand along the major part of its height and will be pressed against the endosteal wall over a large extent, resulting in a good blocking and by the large contact surface also a rigidly fixation is obtained and therefor the bone plug can resist high cement pressures.

To clarify the mechanism of the bone plug in the FIGS. 4 up to 7 inclusive the bone plug 1 is shown in the initial non-compressed and in the compressed expanded condition as well in a longitudinal section as in a perspective view, in which FIGS. 4 and 5 show the initial non-compressed condition and the FIGS. 6 and 7 show the compressed expanded condition.

In the assembled non-compressed condition the body 15 is located between the disc 23 and the ring 31, see FIG. 4 and 5. The ring 31 locks behind one of the protrusions 27. The protrusions 27 are saw-tooth shaped and the inner wall of the hole in ring 31 is bevelled by which ring 31 can lock behind the protrusions of the stem.

In FIGS. 6 and 7 it clearly shows that body 15 expands in the radial direction, when it is compressed in the axial direction. The dimensions of body 15 depend on the size of the cross-section of the canal to be blocked. The size of the body 15 in the longitudinal direction of the stem is called the height of the body. The shape of body 15 is such that the height of the body is at most 6 times the average wall thickness of the body. If the height would be more the body has a tendency to fold and crumple at large axial compression. Preferably the wall thickness of the cylindrical body 15 is in the non-expanded condition (see FIG. 4) at least 0.6 times the wall thickness of the body 15 in the expanded condition (see FIG. 6) in order to get proper blocking of the canal. If the bone plug 1 is present in the canal, the body 15 does not have a cambered shape as is shown in FIG. 6, but a more cylindrical shape like is shown in FIG. 1, such that the wall thickness in the expanded condition is nearly equal along its entire height.

In the FIGS. 8 and 9 further applications of the bone plug are shown. In FIG. 8 a second embodiment of the bone plug 43 according to the invention is shown during surgical use. This bone plug 43 has a hollow stem 45 provided with internal screw thread. A guide wire 47 of an impaction instrument 49 is temporarily screwed into the stem 45. After impaction the instrument 49 can be removed from the canal 51 and the guide wire 47 can be screwed out of the stem of the bone plug 43. In FIG. 9 this bone plug 43 is used to position a prosthetic component 53 inside the intramedullary canal 51. For this purpose the stem 45 does not have to be provided with internal screw thread. The prosthetic component 53 is provided with a tip 55 which fits accurately in the cavity of the stem 45, possibly with a slight press fit.

In FIG. 10 a third embodiment of the bone plug according to the invention is shown in parts. The bone plug 61 has formed a blocking element 63 by a cylindrical body 65 and a first locking element 67 comprising a disc 69 with attached to it a stem 71 provided with saw tooth shaped protrusions 73. The blocking element 63 and the first locking element 67 are identical to the aforementioned embodiments. The bone plug 61 further has a second locking element 75 which differs from the aforementioned embodiments. The second locking element 75 comprises an interrupted ring 77 and an annular plate 79 which in the assembled condition of the bone plug is present between the body 65 and the ring 77.

In the FIGS. 11 and 12 the bone plug 61 is shown in the assembled situation, in respectively a non-compressed and compressed condition. The radial cross-section 81 of ring 77 has in this embodiment a triangular shape, but a ring with a different cross-sectional geometry, for example a circular cross-section, will also function efficiently. The ring 77 is positioned inside a recession 83 in the annular plate 79. The recession 83 is formed by a bevelled edge 85 of the wall of the opening in the plate 79.

In the FIGS. 13 and 14 the bone plug 61 is shown being fixed in the insertion instrument in the non-compressed respectively the compressed expanded condition. The instrument 89 has a tube 91 in which a chuck 93 is movable present. The end 95 of the tube 91 stops the interrupted ring 77 and the annular plate 79 during compression of the body 65. The chuck 93 grips the head 97 of the stem 71 of the first locking element 67 and pulls this into the tube 91, by which the body 65 is compressed in the axial direction and because of this expands in the radial direction, see FIG. 14. The interrupted ring 77 locks with an edge behind one of the protrusions 73 on stem 71.

Although the invention is explained in the aforementioned by means of the drawings, it has to be stated that the invention is in no way limited to the embodiments shown in the drawings. The invention extends to all from the drawings deviant embodiments within the area defined by the claims.

Among others it is possible to execute the body of the blocking element in a cambered or conical shape instead of a cylindrical shape or to give it any other shape. In that case the wall thickness of the body, for defining the desired ratio of the dimensions of the body, is defined as the average wall thickness along the height.

Among others it is also possible to shape the second locking element as an annular plate with an interrupted circular spring of which the diameter of the opening in the annular plate is larger than the diameter of the protrusions on the stem and of which the annular ring is positioned between the circular spring and the body of the blocking element and of which the spring locks behind one of the protrusions. Further for gripping of the stem, the free end of the stem can be provided with a screw thread instead of a circumferential recession in which case the stem is not gripped by a chuck, but the end of the insertion instrument is provided with a counter screw thread and can be screwed on and off the stem. Also the elastomeric material of the body of the blocking element can be manufactured mainly out of silicone.

What is claimed is:

1. A bone plug, for blocking of a canal in a bone, comprising a radially expandable blocking element comprising
   a) an at least nearly solid body, having a height and an average wall thickness along said height, and a continuous axial opening, which body, under axial compression expands in a radial direction, and
   b) locking means to keep the body under axial compression, said means comprising first and second locking elements, in between which the body is positioned,
   i) said first locking element comprising a disc attached to a stem which protrudes through the axial opening of the body, which stem is provided with a number of radial protrusions positioned next to each other in axial direction on the stem, and,
   ii) said second locking element comprising means, positioned around the protruding stem of the first locking element, which may be locked behind one of the protrusions of the stem of the first locking element, whereby the two locking elements may be fixed at various distances to each other,
   the improvement wherein over the whole height of the body the cross-section of the axial opening is equal to or slightly larger than the that of the stem, and the height of the body is at most 8 times the average wall thickness of the body.

2. Bone plug according to claim 1, wherein the height of the body is at most 7 times the average wall thickness of the body.

3. Bone plug according to claim 2, wherein the height of the body is at most 6 times the average wall thickness of the body.

4. Bone plug according to claim 3, wherein the height of the body is at most 5 times the average wall thickness of the body.

5. one plug according to claim 1, wherein the radial protrusions are located at least near to each other in the longitudinal direction of the stem.

6. Bone plug according to claim 1, wherein the radial protrusions have an at least nearly saw tooth shape in a longitudinal section of the stem.

7. Bone plug according to claim 1, wherein the material of the body of the blocking element has at least nearly elastomeric properties.

8. Bone plug according to claim 1, wherein the material of the blocking element is composed mainly from a mixture of gelatine, glycerol and water.

9. Bone plug according to claim 1, wherein the material of the locking elements is mainly made out of polymethylmethacrylate.

10. Bone plug according to claim 1, wherein the second locking element comprises an interrupted ring.

11. Bone plug according to claim 1, wherein the second locking element also comprises an annular shaped plate which is positioned between the body and the interrupted ring.

12. Bone plug according to claim 11, wherein the annular shaped plate has a recession in which the interrupted ring is positioned.

13. Bone plug according to claim 12, wherein the recession in the plate is formed by a bevelled edge of the wall of the opening in the plate.

14. Bone plug according to claim 1, wherein the stem of the first locking element is hollow and is in any case open at is free end.

15. Bone plug according to claim 1, wherein the stem of the first locking element is at its free and provided with screw thread.

16. Bone plug according to claim 1, wherein the stem of the first locking element is weakened nearby its free end.

* * * * *